US008889422B2

(12) United States Patent
Belongia

(10) Patent No.: US 8,889,422 B2
(45) Date of Patent: Nov. 18, 2014

(54) OPTICAL GAS SENSOR FOR USE WITH ELECTRICAL EQUIPMENT AND METHODS OF ASSEMBLING SAME

(75) Inventor: Robert Francis Belongia, Marietta, GA (US)

(73) Assignee: General Electric Company, Schenectady, NY (US)

(*) Notice: Subject to any disclaimer, the term of this patent is extended or adjusted under 35 U.S.C. 154(b) by 516 days.

(21) Appl. No.: 13/029,903

(22) Filed: Feb. 17, 2011

(65) Prior Publication Data

US 2012/0214249 A1   Aug. 23, 2012

(51) Int. Cl.
*G01N 25/18* (2006.01)
*G01N 21/78* (2006.01)
*G01N 33/00* (2006.01)
*G01N 21/77* (2006.01)
*H01F 27/40* (2006.01)

(52) U.S. Cl.
CPC .......... *G01N 21/783* (2013.01); *G01N 33/005* (2013.01); *G01N 2021/7723* (2013.01); *G01N 33/004* (2013.01); *H01F 2027/404* (2013.01); *G01N 2021/7763* (2013.01); *G01N 2021/775* (2013.01); *G01N 2021/7783* (2013.01)
USPC .............................................. 436/149; 422/88

(58) Field of Classification Search
None
See application file for complete search history.

(56) References Cited

U.S. PATENT DOCUMENTS

| | | | |
|---|---|---|---|
| 3,276,004 A | 9/1966 | Mayo, Jr. et al. | |
| 4,560,444 A | 12/1985 | Polak et al. | |
| 4,661,211 A | 4/1987 | Petty-Weeks | |
| 4,795,536 A | 1/1989 | Young et al. | |
| 5,233,194 A * | 8/1993 | Mauze et al. | 250/341.2 |
| 6,596,236 B2 | 7/2003 | DiMeo, Jr. et al. | |
| 7,852,480 B2 | 12/2010 | Uchiyama | |
| 2005/0186117 A1 | 8/2005 | Uchiyama et al. | |
| 2008/0283388 A1 | 11/2008 | Yamamoto et al. | |

FOREIGN PATENT DOCUMENTS

| | | |
|---|---|---|
| DE | 195 03 802 C1 | 3/1996 |
| DE | 10 2008 023 482 A1 | 11/2008 |
| EP | 0 120 203 A1 | 10/1984 |

OTHER PUBLICATIONS

Shoureshi, R. et al., Optical Sensor for Transformer Monitering, 2004, PSERC Publication 2004-27, pp. 1-22.*
Search Report issued in connection with EP Patent Application No. 12155229.3, May 7, 2012.

* cited by examiner

*Primary Examiner* — Robert Xu
(74) *Attorney, Agent, or Firm* — Armstrong Teasdale LLP

(57) ABSTRACT

A method and apparatus for detecting a gas in electrical equipment by coupling a gas detection device to the electrical equipment is provided. The method includes providing an electro-magnetic source, positioning an electro-magnetic detector to receive light emitted from the electro-magnetic source, and positioning a membrane between the electro-magnetic source and the electro-magnetic detector, such that the electro-magnetic detector only receives light from the electro-magnetic source that has been transmitted through the membrane. The method also includes detecting at least one gas, such that detection of at least one gas includes preventing or allowing communication of the electro-magnetic source and the electro-magnetic detector, and emitting a signal, by the electro-magnetic detector, in response to the detection of the at least one gas.

14 Claims, 2 Drawing Sheets

OPTICAL GAS SENSOR FOR USE WITH ELECTRICAL EQUIPMENT AND METHODS OF ASSEMBLING SAME

BACKGROUND OF THE INVENTION

The field of the invention relates generally to an optical gas sensor assembly and more particularly, to an optical gas sensor for use with an electrical transformer.

Generally, as electrical equipment operates, heat is generated that requires the equipment to be cooled to prevent damage to the equipment and/or to components associated with the equipment. Small electrical equipment is often cooled using ambient air directed though fans. Larger electrical equipment often requires additional cooling from a different cooling source such as a dielectric fluid. For example, at least some known power transformers use oil to insulate windings and to aid in the transfer of electrical energy from one circuit to another. In such transformers, often, hydrocarbon or mineral-based oils, and/or silicone-based oils are used as cooling fluid because of the high dielectric strength, heat transfer properties, and chemical stability of such fluids.

Under normal operating conditions, generally very little decomposition of the dielectric fluid occurs. However, when a thermal or electrical fault develops, dielectric fluid and/or solid insulation may begin to decompose. Moreover, as the insulating materials of a transformer break down from excessive thermal and/or electrical stresses, for example, gaseous bi-products form that may be soluble in the dielectric fluid. Analysis of the quantity or concentration of each of the fault gases present in the fluid enables fault processes such as corona, sparking, overheating, and arcing to be identified. If the insulating materials breakdown, over time transformers may fail and/or rupture, which may lead to power outages and losses.

To facilitate reducing the costs associated with repairing transformers and restoring power outages, at least some known detection systems are used in an attempt to more accurately predict transformer breakdowns. For example, at least some known methods of detecting and preventing transformer outages use a Buchholz relay to detect gas evolved during internal arcing, and to enable the transformer to be rapidly de-energized to avert catastrophic failure. However, the costs of such relays may limit their use.

BRIEF DESCRIPTION OF THE INVENTION

In one aspect, a method for detecting a gaseous bi-product in electrical equipment by coupling a gas detection device to the electrical equipment is provided. The method includes providing an electro-magnetic source, positioning an electro-magnetic detector to receive light emitted from the electro-magnetic source, and positioning a membrane between the electro-magnetic source and the electro-magnetic detector, such that the electro-magnetic detector only receives light from the electro-magnetic source that has been transmitted through the membrane. The method also includes detecting at least one gas, such that detection of at least one gas includes preventing or allowing communication of the electro-magnetic source and the electro-magnetic detector, and emitting a signal, by the electro-magnetic detector, in response to the detection of the at least one gas.

In another aspect, a light sealed apparatus for detecting a gaseous bi-product of electrical equipment is provided. The apparatus includes a light source, a photocell, and a membrane interposed between said light source and said photocell, such that interaction of said membrane and a gaseous bi-product prevents or allows light communication between said light source and said photocell.

In yet another aspect, a system for detecting gaseous bi-products of electrical equipment is provided. The system includes an oil-cooled electrical apparatus and a light sealed apparatus coupled to the oil-cooled electrical apparatus, such that the light sealed apparatus is configured to detect a gaseous bi-product of the oil-cooled electrical apparatus. The light sealed apparatus includes a light source, a photocell, and a membrane interposed between said light source and said photocell, such that interaction of said membrane and a gaseous bi-product prevents or allows light communication between said light source and said photocell.

DETAILED DESCRIPTION OF THE INVENTION

Figure 1:
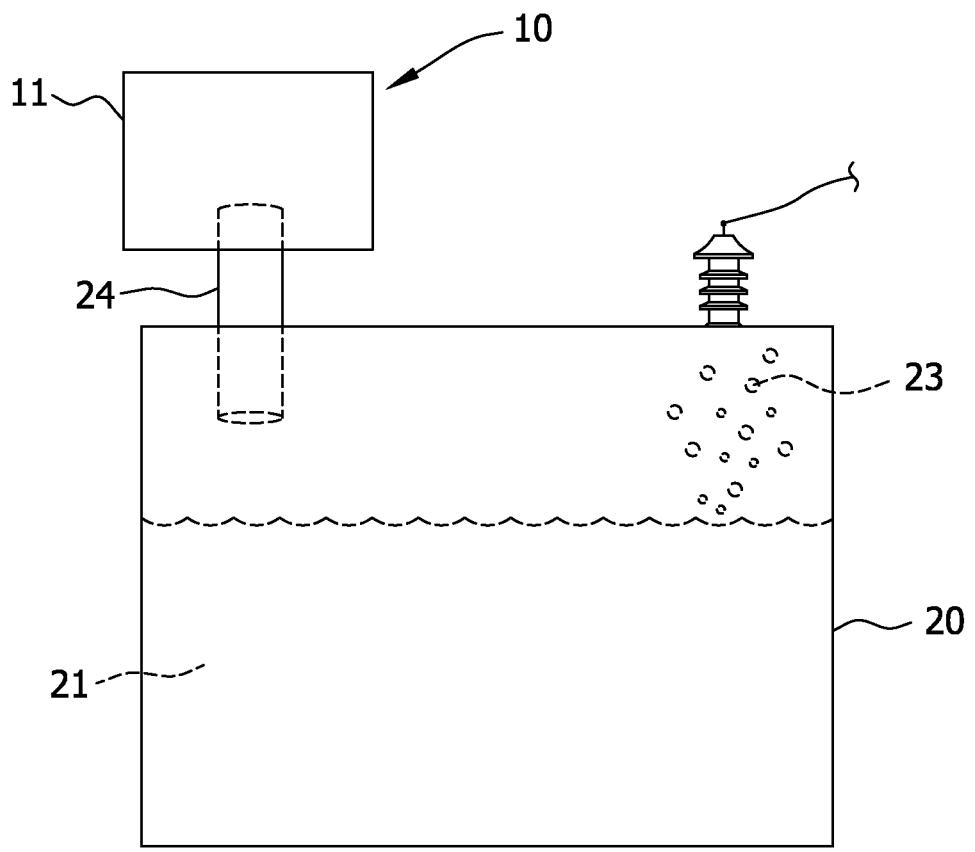
FIG. 1 is a schematic representation of an exemplary monitoring system that may be used to monitor gases released from an oil-cooled transformer.
Figure 2:
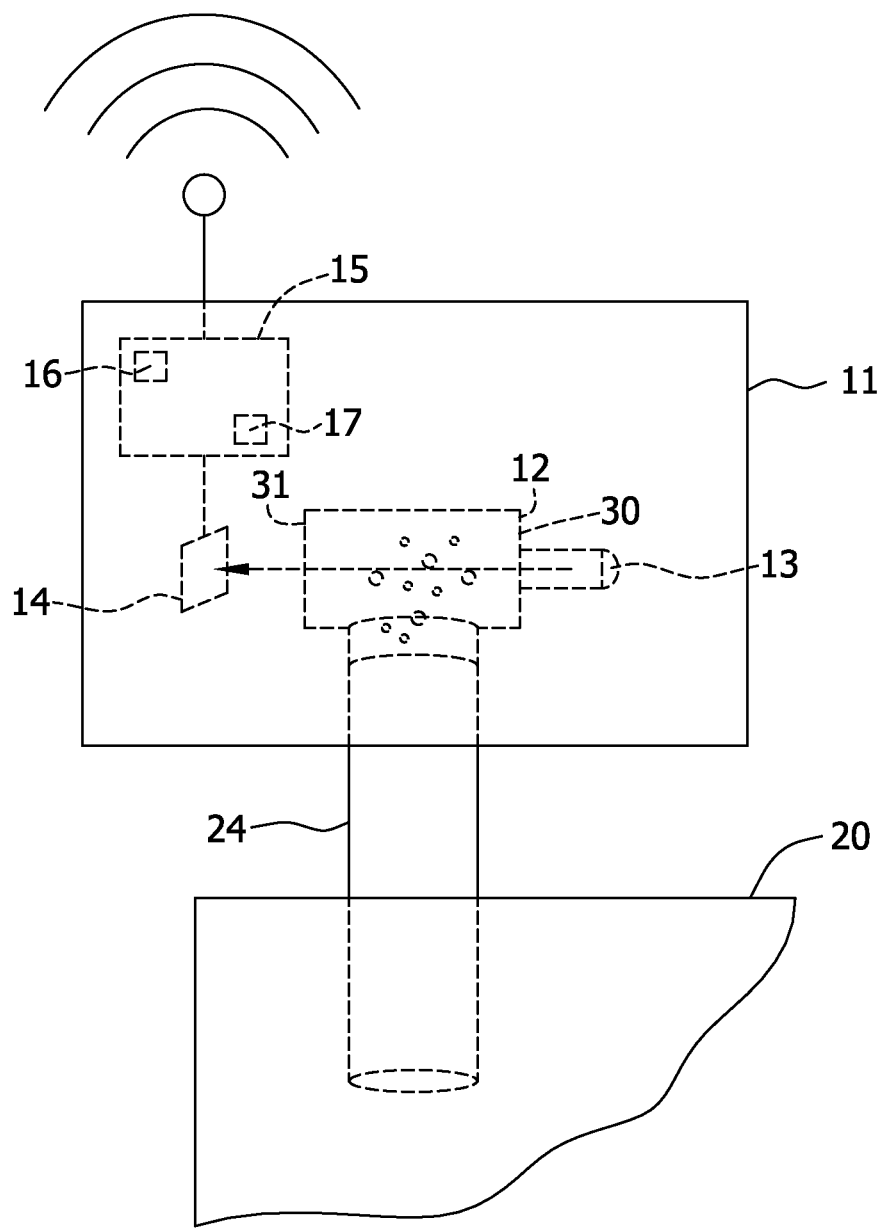
FIG. 2 is a schematic view of the monitoring system shown in FIG. 1.

FIG. 1 is a schematic representation of a system 10 that may be used to monitor gases released from electrical equipment, such as an oil-cooled transformer 20. FIG. 2 is a schematic view of monitoring system 10 shown in FIG. 1. In the exemplary embodiment, system 10 is coupled to transformer 20 via a conduit 24. Moreover, in the exemplary embodiment, transformer 20 includes an oil-cooled system 10 that circulates oil 21 throughout transformer 20 to facilitate removing heat generated within transformer 20 and to facilitate preventing electrical breakdown under load within transformer 20. For example, oil 21 is a mineral oil that is circulated within transformer 20 to facilitate cooling of transformer 20. Alternatively, any other fluid may be circulated within transformer 20 that enables transformer 20 to function as described herein.

In the exemplary embodiment, during operation, over time, oil 21 circulated in transformer 20 may eventually degrade and break down. During the degradation process, gases or gaseous bi-products 23 are released into transformer 20 as internal arcing occurs. For example, within some known transformers, hydrogen gas may be released during oil 21 breakdown. Over time, depending on the degradation of oil 21, continued operation with degraded oil 21 may cause transformers 20 to fail, rupture, and/or overheat.

Monitoring system 10, in the exemplary embodiment, includes a housing 11, and is coupled to transformer 20 via conduit 24. Housing 11 includes a membrane 12, an electro-magnetic or light source 13, and an electro-magnetic detector or photocell 14. Membrane 12 extends between light source 13 and corresponding photocell 14, such that conduit 24 is in flow communication with membrane 12. Photocell 14 is electrically coupled to a digital converter 15 that includes a processor 16 and a transmitter 17 that can be active or passive, e.g. RFID.

In the exemplary embodiment, membrane 12 is releasably coupled within system 10 to enable membrane 12 to be replaced without requiring other components within system 10 to be removed from system 10 and/or disassembled. Moreover, in the exemplary embodiment, membrane 12 is substantially translucent to a specific wavelength or frequency in the visible or near visible light spectrum, such that light passes therethrough. Furthermore, in the exemplary embodiment, membrane 12 is fabricated from a material that reacts to gaseous bi-products 23 of a transformer 20 such as, but not limited to, a membrane material including at least one of a lead acetate and sulfur. Alternatively, membrane 12 may be fabricated from any material that enables membrane 12 to react with any gaseous bi-product produced as the cooling fluid within transformer 20 breaks down, and that enables the monitoring system to function as described herein.

As gases 23 enter system 10, the gases 23 react with membrane 12 and cause membrane 12 to become substantially opaque or translucent to a wavelength in the visible or near visible spectrum of light. In an alternative embodiment, membrane 12 may be designed to become substantially opaque to any wave of light on the electrometric scale including, but not limited to, radio waves, microwaves, infrared waves, visible light waves, ultraviolet waves, X-rays, and/or gamma rays. For example, in the exemplary embodiment, hydrogen gas enters system 10 from transformer 20, the hydrogen gas reacts with membrane 12 and membrane 12 becomes substantially opaque to visible light, thus preventing the transmission of light from light source 13 to photocell 14. It should be noted that the material used in fabricating membrane 12 may be variably selected to react with elements other than hydrogen. In one embodiment, membrane 12 is configured to become substantially opaque or translucent in response to a predetermined concentration or quantity level of gaseous bi-products 23.

For example, in one embodiment, membrane 12 is selected to react with multiple gaseous bi-products 23, such that each gaseous interaction with membrane 12 renders membrane 12 substantially opaque to different waves. For example, membrane 12 may react with hydrogen to render membrane 12 substantially opaque to red visible light, while a reaction with carbon dioxide may render membrane 12 substantially opaque to green visible light. In another embodiment, membrane 12 is porous to enable gas 23 to pass through membrane 12. More specifically, in such an embodiment, gas 23 passing through membrane 12 is trapped and causes membrane 12 to swell until substantially all communication between light source 13 and photocell 14 is blocked. Alternatively, membrane 12 may react with a first gas, such as hydrogen, to render membrane 12 substantially opaque to ultraviolet light waves and have a different reaction with a second gas that is different than the first gas, such as carbon dioxide. In such an embodiment, a reaction with carbon dioxide may render membrane 12 substantially opaque to infrared light waves.

In an alternative embodiment, membrane 12 is selected to substantially prevent any waves to be transmitted through membrane 12 before being introduced into system 10. In such an embodiment, gases 23 interact with membrane 12 to render membrane 12 substantially translucent, thus enabling waves to pass through membrane 12.

In the exemplary embodiment, light source 13 is positioned on a first side 30 of membrane 12, and photocell 14 is located on an opposite or second side 31 of membrane 12. Light source 13 and photocell 14 are oriented such that light emitted from light source 13 passes through membrane 12 before it is received at photocell 14. In the exemplary embodiment, light source 13 is a light emitting diode (LED) light. Alternatively, light source 13, may be any other light source, such as but not limited to, an organic LED (OLED) source, an incandescent source, a fluorescent source, and a halogen source, and/or any other light source that enables system 10 to function as described herein. Moreover, light source 13 may emit any color of light including, but not limited to, green, blue, red, and/or white light, and photocell 14 can include a colorimeter to detect the presence or absence of particular wavelengths. Alternatively, light source 13, may emit light at the same or different wave lengths through membrane 12 towards photocell 14.

Photocell 14 is coupled to digital converter 15 in an orientation that enables photocell 14 to receive light emitted from light source 13. More specifically, in the exemplary embodiment, photocell 14 is selected to detect a desired light color and/or a wavelength of light being emitted from light source 13. Moreover, in the exemplary embodiment, if light is not detected by photocell 14, an electrical signal is transmitted by photocell 14 to converter 15 for processing. In an alternative embodiment, photocell 14 receives light emitted from multiple light sources 13 and photocell 14 transmits an electrical signal if any loss of communication, i.e., photocell 14 stops receiving light emitted from any source 13, with any respective light source 13 occurs. For example, if photocell 14 is in communication with an ultraviolet light wave, an infrared wave, a blue visible light wave, and a green visible light wave, photocell 14 is configured to transmit an electrical signal to converter 15 whether photocell 14 stops receiving any light of a specified wave emitted from source 13.

Digital converter 15 is electrically coupled with photocell 14 and transmitter 17. Converter 15 processes and decodes signals transmitted from photocell 14, via a processor 16. More specifically, in the exemplary embodiment, transmitter 17 transmits a processed signal to a source external to system 10 indicative of at least one of a presence, a concentration, and a quantity of predetermined gases 23. In one embodiment, transmitter 17 indicates a lead time to failure using the information provided by converter 15 and processor 16. In another embodiment, transmitter 17 indicates a failure of electrical equipment, such as transformer 20, using the information provided by converter 15 and processor 16

For example, in the exemplary embodiment, transmitter 17 transmits a signal wirelessly to a device configured to receive the signal. For example, in one embodiment, such an external device may include, but is not limited to only including, a cellular device and a computer. Alternatively, digital convertor may be coupled to a display (not shown) that displays the decoded signals received from photocell 14 in a manner visible by a user.

The exemplary methods and systems described herein facilitate detection of gaseous bi-products formed from the breakdown of dielectric fluid used in electrical equipment. By detecting gaseous bi-products, the exemplary methods and systems enable the electrical equipment to be repaired to avoid a failure and/or rupture of the electrical equipment, which may lead to power outages and losses, therefore, increasing an operating life of the electrical equipment. Additionally, the methods and systems described herein provide a cost effective alternative to known detection systems, which can be cost prohibitive.

Exemplary embodiments of an optical gas sensor assembly for use in electrical equipment and method of assembling same are described above in detail. The methods and systems are not limited to the specific embodiments described herein, but rather, components of systems and/or steps of the methods may be utilized independently and separately from other components and/or steps described herein. For example, the methods may also be used in combination with other electrical systems and methods, and are not limited to practice with only the oil-cooled electrical systems and methods as described herein. Rather, the exemplary embodiment may be implemented and utilized in connection with many other electrical applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for detecting gas in electrical equipment, said method comprises:
   providing an electro-magnetic source;
   positioning an electro-magnetic detector to receive light emitted from the electro-magnetic source;
   positioning a membrane between the electro-magnetic source and the electro-magnetic detector, such that the electro-magnetic detector only receives light from the electro-magnetic source that has been transmitted through the membrane, wherein the membrane is chemically reactive to a plurality of types of gases;
   detecting at least one of the plurality of types of gases by detecting a variation of a characteristic of the light through the membrane, and by identifying a type of gas of the plurality of types of gases associated with the at least one gas based at least in part on the variation; and
   emitting a signal, by the electro-magnetic detector, in response to the detection of the at least one gas.

2. A method in accordance with claim 1, further comprising electrically coupling a digital converter to the electro-magnetic detector, such that the digital converter is configured to convert signals from the electro-magnetic detector.

3. A method in accordance with claim 2, further comprising emitting a converted signal.

4. A method in accordance with claim 3, wherein emitting a converted signal comprises emitting a converted signal wirelessly.

5. A method in accordance with claim 1, wherein the signal is displayed outside the gas detection device.

6. A method in accordance with claim 1, wherein providing an electro-magnetic source comprises providing an electro-magnetic source that is at least one of a visible light, an infrared light, and an ultraviolet light, and combinations thereof 7. A method in accordance with claim 6, wherein providing an electro-magnetic source comprises providing a plurality of electro-magnetic sources.

8. An apparatus for use in detecting gaseous bi-products in electrical equipment, said apparatus comprising:
   a light source;
   a photocell; and
   a membrane that is chemically reactive to a plurality of gaseous bi-products, wherein said membrane is interposed between said light source and said photocell, such that interaction of said membrane and a gaseous bi-product varies a characteristic of light communication between said light source and said photocell, said photocell is configured to identify a type of the gaseous bi-product based at least in part on the variation of the light communication.

9. An apparatus in accordance with claim 8, further comprising a digital converter configured to convert electrical signals from said photocell.

10. An apparatus in accordance with claim 9, further comprising a transmitter configured to transmit an indication that a gaseous bi-product is detected.

11. An apparatus in accordance with claim 10, such that said transmitter is a wireless transmitter.

12. An apparatus in accordance with claim 8, such that said light source is at least one of a visible light, an infrared light, and an ultraviolet light.

13. An apparatus in accordance with claim 8, such that said light source is a plurality of light sources.

14. An apparatus in accordance with claim 8, wherein the gaseous bi-product is Hydrogen gas.

* * * * *

UNITED STATES PATENT AND TRADEMARK OFFICE
CERTIFICATE OF CORRECTION

PATENT NO. : 8,889,422 B2  
APPLICATION NO. : 13/029903  
DATED : November 18, 2014  
INVENTOR(S) : Robert Francis Belongia Page 1 of 1

It is certified that error appears in the above-identified patent and that said Letters Patent is hereby corrected as shown below:

On the title page, item 56 under OTHER PUBLICATIONS, delete "Monitering" and insert therefor -- Monitoring --.

In the claims
In Claim 6, column 6, line 10, delete "thereof" and insert therefor -- thereof. --.

Signed and Sealed this
Fourteenth Day of June, 2016

Michelle K. Lee
*Director of the United States Patent and Trademark Office*